United States Patent
Bombardelli et al.

(10) Patent No.: US 8,496,975 B2
(45) Date of Patent: Jul. 30, 2013

(54) COMPOSITIONS FOR THE TREATMENT AND PREVENTION OF INFECTIONS OF THE ORAL CAVITY

(75) Inventors: Ezio Bombardelli, Gropello Cairoli (IT); Gabriele Fontana, Milan (IT); Andrea Giori, Milan (IT); Paolo Morazzoni, Milan (IT); Antonella Riva, Milan (IT); Massimo Ronchi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/988,870

(22) PCT Filed: Apr. 6, 2009

(86) PCT No.: PCT/EP2009/002515
§ 371 (c)(1), (2), (4) Date: Dec. 14, 2010

(87) PCT Pub. No.: WO2009/129926
PCT Pub. Date: Oct. 29, 2009

(65) Prior Publication Data
US 2011/0091392 A1    Apr. 21, 2011

(30) Foreign Application Priority Data

Apr. 24, 2008 (IT) .............................. MI2008A0746
Jun. 12, 2008 (EP) .................................... 08425422

(51) Int. Cl.
| | | |
|---|---|---|
| A61K 9/68 | (2006.01) | |
| A61K 31/4355 | (2006.01) | |
| A61K 8/49 | (2006.01) | |
| A61P 1/02 | (2006.01) | |

(52) U.S. Cl.
USPC ............. 424/725; 424/58; 424/734; 424/749; 424/776; 424/777; 424/778; 424/779

(58) Field of Classification Search
USPC .................................................. 424/54, 729
See application file for complete search history.

(56) References Cited

U.S. PATENT DOCUMENTS

| | | |
|---|---|---|
| 4,908,211 A | 3/1990 | Paz |
| 5,066,483 A | 11/1991 | Harkrader et al. |
| 2006/0141073 A1* | 6/2006 | Worrell et al. ................ 424/729 |

FOREIGN PATENT DOCUMENTS

| | | |
|---|---|---|
| EP | 0 297 535 | 1/1989 |
| EP | 0 464 297 | 1/1992 |
| JP | 63 267714 | 11/1988 |

* cited by examiner

*Primary Examiner* — Walter Webb
(74) *Attorney, Agent, or Firm* — Lucas & Mercanti, LLP

(57) ABSTRACT

The present invention relates to compositions comprising benzophenanthridine alkaloids, benzofuran compounds and catechin polyphenols, which are useful in the treatment and prevention of infections of the oral cavity.

12 Claims, No Drawings

COMPOSITIONS FOR THE TREATMENT AND PREVENTION OF INFECTIONS OF THE ORAL CAVITY

SUMMARY

The present invention relates to compositions comprising benzophenanthridine alkaloids, benzofuran compounds and catechin polyphenols, which are useful in the treatment and prevention of infections of the oral cavity.

The compositions of the present invention possess antibacterial, antifungal and antienzymatic activities, which are useful in oral hygiene and the treatment and prevention of pathological forms of various origins associated with the dentition, implants and complications of surgery of the oral cavity.

Said compositions can be administered in the form of tablets that dissolve slowly in the oral cavity, or in the form of a mouthwash or chewing gum.

PRIOR ART

The formation of bacterial or fungal films in the mouth very often gives rise to disorders such as tooth decay, pyorrhoea and periodontal and gingival infections. In particular, the formation of bacterial or fungal films is very common in implantology, denture maintenance, and elderly dental patients in general.

It has been reported in the literature that benzophenanthridine alkaloids possess antibacterial and antifungal activity, in particular against Gram+ bacteria, and are able to rupture the bacterial film, thus making the pathogen sensitive to bacteriostatic compounds or antibiotics.

Benzofuran compounds with a neolignan structure are also known to inhibit the formation of bacterial and fungal films or rupture films already formed, thus preventing their re-formation; such compounds are found in extracts of *Krameria triandra, Eupomatia laurina* and *Piper* sp, in particular eupomatenoids and 2-(2',4'-dihydroxyphenyl)-5-propenylbenzofuran.

Enzymes such as α-amylase, glucosidase and takadiastase which are present in the oral cavity promote the breakdown of carbohydrates; however, this leads to the formation of glucose which is very harmful to oral hygiene because it contributes to the formation of bacterial film in the oral cavity. Inhibitors of these enzymes therefore help to prevent the formation of the bacterial film.

Procyanidins, in particular catechin oligomers esterified with gallic acid, are glucosidase and takadiastase inhibitors.

The polyphenols extracted from *Vitis vinifera* are powerful inhibitors of α-amylase and glucosidase.

DESCRIPTION OF THE INVENTION

The present invention relates to compositions comprising:
a) benzophenanthridine alkaloids;
b) benzofuran compounds; and
c) catechin polyphenols;
with antibacterial, antifungal and antienzymatic activities, which reduce the formation of bacterial and fungal films in the oral cavity, thus reducing halitosis and the formation of dental plaque.

The preferred benzophenanthridine alkaloids are chelerythrine and sanguinarine, while the preferred benzofuran compounds are compounds with a neolignan structure, found in extracts of *Krameria triandra, Eupomatia laurina* and *Piper* sp, in particular eupomatenoids and 2-(2',4'-dihydroxyphenyl)-5-propenylbenzofuran.

According to the invention, the benzofuran compounds have the following formula

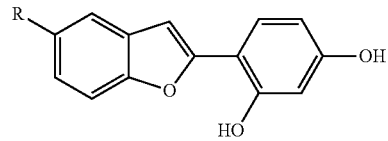

where R may be hydrogen or a linear or branched alkyl chain with 2 to 6 carbon atoms, or an alkyl chain substituted by amino, nitro groups; R is preferably hydrogen or C1-C3 alkyl.

Said benzofuran compounds are known and can be prepared by conventional methods, for example by reaction of a phenol suitably substituted with 2-phenoxy-2',4'-dimethoxyacetophenone in the conditions reported in Chimie Therapeutique 1973, 8, 398, followed by cyclisation in the presence of polyphosphoric acid in xylene and hydrolysis of the methoxy and hydroxy groups.

It has now surprisingly been found that the compositions according to the invention possess an extremely powerful antibacterial, antifungal and antienzymatic activity, greater than that obtained from the sum of the various components administered separately. Said effect may be due to a synergistic action mechanism which takes place between the various components of the association in question.

The compositions according to the invention are therefore useful in oral hygiene and in the treatment and prevention of pathological forms of various origins associated with the dentition, implantology and complications of surgery of the oral cavity.

More particularly, the present invention relates to compositions comprising:
a) benzophenanthridine alkaloids selected from sanguinarine and/or chelerythrine and/or derivatives thereof;
b) benzofuran compounds as defined above;
c) monomeric or oligomeric catechin polyphenols.

According to the invention, the compositions will contain the various components in the following intervals (by weight per unit dose):
a) benzophenanthridine alkaloids: from 0.5 mg to 10 mg;
b) benzofuran: from 5 to 25 mg;
c) polyphenol compounds: from 10 to 100 mg.

According to a particularly preferred aspect, the compositions will contain the various components within the following intervals (by weight per unit dose):
a) benzophenanthridine alkaloids: from 2.5 to 5 mg;
b) benzofuran compounds: from 3 to 10 mg;
c) polyphenol compounds: from 40 to 50 mg.

The benzophenanthridine alkaloids sanguinarine and chelerythrine may be present in the free or salified form, as such in substantially pure form or in the form of extracts of *Sanguinaria canadensis, Macleaya cordata* or *Macleaya macrocarpa*. According to a preferred aspect, the benzophenanthridine alkaloids will be present in a form salified with luteic acid. Said salts, which are prepared by reacting the sulphates or chlorides of the alkaloids with the sodium or potassium salt of luteic acid and subsequent crystallisation, have proved particularly effective for the purposes of the present invention.

The compounds with a benzofuran structure described above may be present as such or in the form of extracts containing them, such as extracts of *Krameria triandra, Eupomatia laurina* and *Piper* sp. The compounds isolated from *Krameria triandra* which have proved particularly active are Eupomatenoid 6 and neolignan 2-(2,4-dihydroxyphenyl)-5-(E)-propenyl-benzofuran, which have demonstrated antibacterial and antifungal activity on numerous strains of Gram+ bacteria, fungi and anaerobic bacteria.

The polyphenol compounds may be present in the form of monomer units such as catechin, epicatechin and gallocatechin and its gallic esters at the C3 hydroxyl, or oligomeric units, preferably up to five units. According to a particularly preferred aspect, the oligomer units will be esterified with gallic acid in C3. The polyphenol compounds may also be present in the form of extracts of seeds or aerial parts of *Vitis vinifera, Aesculus hippocastanum, Camellia sinensis, Theobroma cacao* and the like. These compounds are particularly indicated in oral hygiene, halitosis and gingival infections.

The compositions according to the invention will be conveniently formulated as melt-in-the-mouth tablets, mouthwashes, gels for dispersal in the oral cavity, chewing gums and the like. Said formulations can be prepared according to well-known conventional methods, such as those described in "Remington's Pharmaceutical Handbook", Mack Publishing Co., N.Y., USA, together with suitable excipients.

The formulations according to the invention will be administered to patients up to 5 times in 24 hours for several days, depending on the disorder to be treated. For oral hygiene alone, the number of administrations could be reduced to 2, taken at main meals.

The examples set out below illustrate the invention, without limiting its scope.

EXAMPLE 1

Preparation of Benzofuran Compounds

Step A. Preparation of 2-phenoxy-2',4'-dimethoxyacetophenone (a)

A solution of 2-bromo-2',4'-dimethoxyacetophenone (5 g, 19.1 mmols) in 25 mL of 2-butanone was added to a suspension of phenol (1.8 g, 19.1 mmols), $K_2CO_3$ (2.6 g, 19.1 mmols) and KI (41.5 mg, 0.25 mmols) in 20.0 mL of the same solvent. The solution was then refluxed for 20 hours. The mixture was filtered and the solvent was evaporated off under vacuum. The residue obtained was dissolved in EtOAc and washed with a 10% aqueous solution of NaOH and then with water. The organic extract was dried over $Na_2SO_4$, filtered and evaporated under vacuum. Finally, the crude residue was washed with $Et_2O$ and dried under low pressure to provide 4.4 g (yield: 84%) of the title compound.

Step B. Preparation of 2-(2',4'-dimethoxyphenyl)benzofuran (b)

12 g of polyphosphoric acid was added to a solution of the compound obtained at Step A (4.4 g, 16.2 mmols) in 130.0 mL of xylene. The mixture was refluxed for 2 hours, and then left to cool at room temperature. The solution was then decanted and evaporated under low pressure. The resulting residue (3.7 g, yield: 90%) was used in the next step without further purification.

Step C. Preparation of -(2',4'-dihydroxyphenyl)benzofuran (1)

A mixture of the compound prepared at Step B (3.7 g, 14.5 mmols) and pyridine hydrochloride (11.1 g, 96.4 mmols) was heated to 225° C. for 45 minutes. The red product formed was poured into 10% HCl. The mixture was washed repeatedly with EtOAc; the combined organic layers were dried over $Na_2SO_4$ and evaporated. The residue was purified by column chromatography (hexane/EtOAc=7:3) to provide. The final compound was obtained in a 41% yield (1.36 g) after crystallisation from benzene.

FORMULATION EXAMPLE 1

Melt-in-the-Mouth Tablets

| | |
|---|---|
| Benzophenanthridine alkaloid | 2.5 mg |
| Benzofuran compound | 10.0 mg |
| Extract of *Vitis vinifera* | 50.0 mg |
| Xylitol | 500.0 mg |
| Mannitol | 400.0 mg |
| Liquorice flavouring | 50.0 mg |
| Magnesium stearate | 10.0 mg |
| Acesulfame K | 5.0 mg |

FORMULATION EXAMPLE 2

Oral Gel

| | |
|---|---|
| Benzophenanthridine alkaloid | 3.0 mg |
| Benzofuran compound | 10.0 mg |
| Extract of *Camellia sinensis* | 50.0 mg |
| Glycerin | 400.0 mg |
| Liquid sorbitol | 200.0 mg |
| Hydroxyethylcellulose | 30.0 mg |
| Mint flavouring | 20.0 mg |
| Methyl para-hydroxy benzoate | 10.0 mg |
| Acesulfame K | 5.0 mg |
| Purified water q.s. to | 2.0 g |

The invention claimed is:

1. Compositions comprising by weight per unit dose:
a) benzophenanthridine alkaloids from 0.5 mg to 10 mg;
b) benzofuran compounds of formula

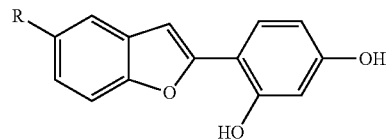

from 5 mg to 25 mg,
where R may be hydrogen or a linear or branched alkyl chain with 2 to 6 carbon atoms, or an alkyl chain substituted by amino, nitro groups; and
c) catechin polyphenols from 10 mg to 100 mg.

2. Compositions as claimed in claim 1, further comprising the benzofuran compounds or benzofuran-containing extracts wherein the benzophenanthridine alkaloids are selected from sanguinarine and/or chelerythrine and/or derivatives thereof, and wherein the catechin polyphenols are monomeric or oligomeric.

3. Compositions as claimed in claim 2, wherein by weight per unit dose:
a) benzophenanthridine alkaloids are present from 2.5 to 5 mg;

b) benzofuran compounds are present from 3 to 10 mg; and
c) polyphenol compounds are present from 40 to 50 mg.

4. Compositions as claimed in claim 2, wherein the benzophenanthridine alkaloids sanguinarine and chelerythrine are present in the free or salified form, in substantially pure form or as extracts of *Sanguinaria canadensis, Macleaya cordata* or *Macleaya macrocarpa*.

5. Compositions as claimed in claim 4, wherein the benzophenanthridine alkaloids are salified with luteic acid.

6. Compositions as claimed in claim 1, wherein the benzofuran compounds of formula 1 are present as benzofuran-containing extracts.

7. Compositions as claimed in claim 6, wherein the benzofuran-containing extracts are extracts of *Krameria triandra, Eupomatia laurina* and *Piper sp.*

8. Compositions as claimed in claim 1, wherein the polyphenol compounds are monomer units such as catechin, epicatechin and gallocatechin and its gallic esters at the C3 hydroxyl, or oligomer units.

9. Compositions as claimed in claim 8, wherein the polyphenol compounds are extracts of seeds or aerial parts of *Vitis vinifera, Aesculus hippocastanum, Camellia sinensis* or *Theobroma cacao*.

10. Formulations as claimed in claim 1, in the form of melt-in-the-mouth tablets, mouthwashes, gels to be dispersed in the oral cavity, or chewing gums.

11. Method of treatment of disorders of the oral cavity comprising preparing oral formulations for oral hygiene comprising an effective amount of
   a) benzophenanthridine alkaloids;
   b) benzofuran compounds; and
   c) catechin polyphenols; and
   administering said formulations to a patient in need thereof and treating said patients wherein said effective amount comprises by weight per unit dose from about 0.5 mg to 10 mg of benzophenathridine alkaloids, from 5 mg to 25 mg of benzofuran compounds and from 10 mg to 100 mg of polyphenols.

12. The method as claimed in claim 11, wherein the disorders of the oral cavity are pathological forms associated with the dentition, implants or complications of surgery of the oral cavity.

* * * * *